United States Patent [19]

Nguyen et al.

[11] Patent Number: 5,177,234

[45] Date of Patent: Jan. 5, 1993

[54] PREPARATION OF ALKOXYSILANES BY CONTACTING A SOLUTION OF HYDROGEN FLUORIDE IN AN ALCOHOL WITH SILICON

[75] Inventors: Binh T. Nguyen; John L. Speier, both of Midland, Mich.

[73] Assignee: Dow Corning Corporation, Midland, Mich.

[21] Appl. No.: 709,056

[22] Filed: Jun. 3, 1991

[51] Int. Cl.⁵ .............................. C07F 7/04; C07F 7/18
[52] U.S. Cl. ...................................................... 556/470
[58] Field of Search ......................................... 556/470

[56] References Cited

U.S. PATENT DOCUMENTS

| | | | |
|---|---|---|---|
| 2,473,260 | 6/1949 | Rochow | 260/448.8 |
| 3,072,700 | 1/1963 | deWit | 260/448.8 |
| 3,505,379 | 4/1970 | Bonitz | 260/448.8 |
| 3,641,077 | 2/1972 | Rochow | 556/470 |
| 3,775,457 | 11/1973 | Muraka | 260/448.8 |
| 4,701,289 | 10/1987 | Liles | 264/8 |
| 4,727,173 | 3/1987 | Medicino | |
| 4,752,647 | 6/1988 | Inaba et al. | 556/470 |
| 4,762,939 | 8/1988 | Medicino | 556/470 |

FOREIGN PATENT DOCUMENTS

| | | |
|---|---|---|
| 0280517 | 8/1988 | European Pat. Off. . |
| 0372918 | 6/1990 | European Pat. Off. . |
| 63-041482 | 2/1988 | Japan . |
| 63-027493 | 5/1988 | Japan . |

*Primary Examiner*—Paul F. Shaver

[57] ABSTRACT

The present invention is a process for preparing alkoxysilanes by the contact of silicon with a solution of hydrogen fluoride in a liquid primary or secondary alcohol. The hydrogen fluoride activates the silicon causing the formation of alkoxysilanes to occur more rapidly and can provide selectivity for the production of dialkoxysilanes and trialkoxysilanes. The process may be run in the presence of copper or a copper compound as a catalyst. The process is advantageously run using atomized silicon.

25 Claims, No Drawings

PREPARATION OF ALKOXYSILANES BY CONTACTING A SOLUTION OF HYDROGEN FLUORIDE IN AN ALCOHOL WITH SILICON

BACKGROUND OF INVENTION

The present invention is a process for preparing alkoxysilanes by the contact of silicon with a solution of hydrogen fluoride in a liquid primary or secondary alcohol. The hydrogen fluoride activates the silicon causing the formation of alkoxysilanes to occur more rapidly and can provide selectivity for the production of dialkoxysilanes and trialkoxysilanes. The process may be run in the presence of copper or a copper compound as a catalyst. The process is advantageously run using atomized silicon.

Silicon is known to react with methanol in the presence of a strong base to form tetramethoxysilane in near quantative yield. For example, Japanese Patent J6-3041-482-A, Feb. 22, 1988, describes a process where silicon is reacted with methanol in the presence of sodium methoxide to form tetramethoxysilane. The process was run at 140° C., for one hour, with the reported yield of tetramethoxysilane being about 95%, based on silicon added to the process. This process does not produce significant quantities of dialkoxysilanes or trialkoxysilanes.

Silicon is also known to react with alcohols in the presence of copper and copper compounds to form alkoxysilanes. Rochow, U.S. Pat. No. 2,473,260, issued Jun. 14, 1949, reports the reaction of silicon with methanol, in the presence of copper or a copper compound, to form a mixture containing 40-50 percent tetramethoxysilane, and polysiloxanes. Typical reaction temperatures for the process were in the range of about 250° C. to 300° C. with contact times of 1.75 to 5.5 hours.

de Wit, U.S. Pat. No. 3,071,700 issued Jan. 8, 1963, describes a process where silicon is reacted with an alcohol in the presence of a copper catalyst, to form dialkoxysilanes and trialkoxysilanes. The process was conducted by passing alcohol vapor through a fluidized-bed of silicon along with an inert carrier gas. The preferred process temperature was reported to be 200° C. to 350° C., with reaction times of 5 to 8 hours. Near quantative conversion of methanol is reported. A similar process is reported in Japanese Patent J6-3027-493-A, May 2, 1988.

Bonitz, U.S. Pat. No. 3,505,379, issued Apr. 7, 1970, describes a process for production of alkoxysilanes where finely divided silicon is reacted in the liquid phase by contact with alcohols or phenols at 20° C. to 300° C. The process is run in the presence of an organic catalyst or metal or metal compound soluble in the liquid phase. The production of mono-, di-, tri-, and tetra-methoxysilanes is reported.

Rochow, U.S. Pat. No. 3,641,077, issued Feb. 8, 1972, describes a process where particulate silicon is suspended in a silicone oil containing a catalyst, such as copper, and an alcohol is introduced beneath the surface of the silicone oil. The process is reported to produce di-, tri-, and tetra-alkoxysilanes. The process was run at a temperature of about 250° C. t 300° C., with contact times of 4-5 hours. Muraoka, U.S. Pat. No. 3,775,457, issued Nov. 27, 1973, reports a similar process where the particulate silicon is suspended in a synthetic oil containing multicyclic aromatic hydrocarbons.

Medicino, U.S. Pat. No. 4,727,173, issued Mar. 31, 1987, reports a process preferential for the production of trialkoxysilane. The process consists of reacting silicon with an alcohol in the presence of a catalytic effective concentration of copper (II) hydroxide.

Medicino, U.S. Pat. No. 4,762,939, issued Aug. 9, 1988, describes a process for producing trialkoxysilane and tetraalkoxysilane mixtures by the direct reaction of silicon with an alcohol in the presence of a copper catalyst. The process is conducted in the presence of mixed solvents, where at least one solvent is inert and at least one other solvent promotes the reaction between trialkoxysilanes and alcohol.

Forwald, EP Application 0-372-918. Pub. Jun. 13, 1990, describes a process for the production of an atomized silicon alloy that is reported to have an improved reaction rate, in comparison to ground silicon, when reacted with an alkylchloride or arylchloride.

The objective of the present invention is to provide a process that can provide significant yields of dialkoxysilanes and trialkoxysilanes at faster rates and shorter reaction times than those previously reported in the literature. This objective is achieved by using a solution of hydrogen fluoride in alcohol to activate the silicon and make the silicon more reactive with the alcohol. The reaction of the activated silicon with the alcohol is further facilitated by the addition of copper or copper compounds to the process as a catalyst. In addition, particulate silicon prepared by atomization has been found to be considerably more reactive in the process than ground particulate silicon.

The alkoxysilanes obtained by the present process contain reactive alkoxy groups and in some cases hydrogen. These reactive constituents make the alkoxysilanes useful as intermediates for preparing various organic silicon compounds or hydride functional polysiloxanes.

SUMMARY OF INVENTION

The present invention is a process for preparing alkoxysilanes by the contact of silicon with a solution of hydrogen fluoride in a primary or secondary alcohol. The hydrogen fluoride activates the silicon causing the formation of alkoxysilanes to occur more rapidly and can provide selectivity for the production of dialkoxysilanes and trialkoxysilanes. The process may be run in the presence of copper or a copper compound as a catalyst. The process is advantageously run using atomized silicon.

DESCRIPTION OF INVENTION

The present invention is a process for preparing alkoxysilanes of formula

$(RO)_n SiH_{4-n}$, where R is a primary or secondary alkyl radical and n=2, 3, or 4. The process comprises: contacting silicon with a solution of hydrogen fluoride in an alcohol of formula

ROH.

where R is as previously described. The process is conducted at a temperature within a range of about 50° C. to 300° C. In an additional embodiment of the present invention, the process may be conducted in the presence of a catalyst selected from the group consisting of copper and copper compounds.

Alkoxysilanes which can be prepared by the present process include, for example, dimethoxysilane, trimethoxysilane, tetramethoxysilane, diethoxysilane, triethoxysilane, tetraethoxysilane, diisopropoxysilane, triisopropoxysilane, tetraisopropoxysilane, dipropoxysilane, tripropoxysilane, tetrapropoxysilane, dibutoxysilane, tributoxysilane, diisobutyoxysilane, triisobutoxysilane, dioctoxysilane, trioctoxysilane, didodecoxysilane, and tridodecoxysilane. The preferred alkoxysilane products are dialkoxysilanes and trialkoxysilanes. Most preferred, is when the alkoxysilane is dimethoxysilane and trimethoxysilane.

The alkoxysilanes are formed by contacting silicon with a solution of hydrogen fluoride in an alcohol. It is preferred that the silicon be of metallurgical grade or greater purity. By metallurgical grade is mant, a silicon mass which contains greater than about 98 percent elemental silicon. The silicon may be in the form of a powder, particles, flakes, chips, or chunks. The physical size and shape of the silicon is not important to the present invention and can be varied within wide limits without significant effect on the process. Preferred is a particulate silicon with a particle size of less than about 60 mesh. Larger particle sizes may be used, but the reduction in available surface area may reduce the rate of product formation. The lower range for particle size is limited only by the ability to produce and handle the particulate silicon. In general, particle sizes greater than about $10\mu$ in diameter are considered useful for the process. The silicon may be alloyed with minor amounts of meals, for example, copper, aluminum, calcium, phosphorus, and zinc. However, no particular advantage is perceived in the instant process for silicon alloys.

Atomized silicon prepared by the method described by Liles, U.S. Pat. No. 4,701,289, issued Oct. 20, 1987, has been found to be particularly active in the described process and is incorporated by reference herein. A preferred atomized silicon is prepared by the method of Liles, where the volatile coolant is water. The inventors believe that the rapid cooling of the atomized silicon creates increased crystal defects which serve as reactive sites for the reaction of silicon with alcohol.

The silicon is contacted with a solution of hydrogen fluoride in liquid alcohol. The solution of hydrogen fluoride a liquid alcohol can be formed by dissolving hydrogen fluoride gas in the liquid alcohol or by adding an acid hydrofluoride salt to the alcohol. By acid hydrofluoride salt, is meant any salt which upon dissolution in the alcohol forms hydrogen fluoride in solution. The acid hydrofluoride salt can be, for example $NH_4F \cdot HF$, $NaF \cdot HF$, and $KF \cdot HF$. Preferred in a solution formed by dissolving hydrogen fluoride gas in a liquid alcohol. The inventors have found that when the solution of hydrogen fluoride in alcohol is formed by this method, the initial induction period observed for the process is shortened, in comparison to when an acid hydrofluoride salt is used to form the solution, and dialkoxysilane is a product.

The inventors postulate that the hydrogen fluoride activates the silicon by removing the oxide coating that forms on silicon, thus making the silicon more readily available for reaction with the alcohol. Therefore, the concentration of hydrogen fluoride is not considered critical and can be varied within a wide range with minimal effect on the rate of the instant process. A useful concentration of hydrogen fluoride in the alcohol is in a range of about 0.01N to 6.0N. A preferred concentration of hydrogen fluoride in the alcohol is within a range of about 0.10N to 1.0N.

The alcohol can be any alcohol of formula ROH, where R is a primary or secondary alkyl radical. Preferred is when R is a primary or secondary alkyl radical of less than 12 carbon atoms. More preferred is when R is a primary or secondary alkyl radical of less than seven carbon atoms. The alcohol can be, for example, methanol, ethanol, propanol, isopropanol, butanol, isobutanol, octanol, and dodecanol. The preferred alcohol is selected from the group consisting of methanol and ethanol, with methanol being most preferred.

Contact of the silicon with the solution of hydrogen fluoride in a liquid alcohol can be effected by standard means for contacting solids and liquids under pressure. The process can be conducted, for example, in a fixed-bed, a stirred-bed, a fluidized-bed, or a vibrating-bed reactor. The process can be conducted as a batch process or a continuous process.

An effective temperature for effecting the reaction of silicon with methanol containing hydrogen fluoride in solution is within a range of about 50° C. to 300° C. A preferred temperature range is about 100° C. to 200° C. The most preferred temperature is in a range of about 130° C. to 170° C.

In the described process, copper and copper compounds can act as a catalyst to facilitate the reaction of the silicon with the hydrogen fluoride containing alcohol solution. The inventors believe that the copper complexes with reactive sites on the silicon to facilitate the reaction of the silicon with the methanol. Therefore, as long as sufficient copper is in solution to saturate the reactive site of the silicon the concentration of copper can be varied within wide limits. The copper can be added to the alcohol as elemental copper or as a copper compound. A useful concentration of copper, either added to the process as elemental copper or as a copper compound, is within a range of about 0.01 to 6.0 weight percent of the silicon. A preferred concentration of copper is within a range of about 1.0 to 3.0 weight percent of the silicon.

The copper compound can be any inorganic or organic compound of copper capable of being reduced to copper in the described process. The inorganic compound of copper can be selected from a group consisting of, for example, copper(I) and copper(II) halides, oxides, sulfates, sulfides, and cyanides. The inorganic compound of copper can be, for example, Cu(I) chloride, Cu(I) bromide, Cu(I) iodide, Cu(I) fluoride, Cu(II) chloride, Cu(II) bromide, Cu(II) iodide, Cu(II) fluoride, Cu(I) oxide, Cu(II) oxide, Cu(I) sulfate, Cu(II) sulfate, Cu(I) sulfide, Cu(II) sulfide, Cu(I) cyanide, Cu(II) cyanide. The preferred inorganic compounds of copper as catalyst for the present process, are copper halides. The preferred copper halide is Cu(I) chloride.

The organic compounds of copper can be for example Cu(II) methoxide, Cu(II) ethoxide, Cu(II) allyloxide, Cu(II) acetate, Cu(II) stearate, Cu(II) tetramethylheptanedionate, Cu(II) acetylacetonate, Cu(II) napthanate, and Cu(II) phenylate.

The preferred copper catalyst for the present process is powdered copper metal with an average particle diameter of less than about $100\mu$.

The following examples are provided to illustrate the practice of the present invention. These examples are not meant to limit the scope of the claims.

EXAMPLE 1

The effects of an acid hydrofluoride salt and a copper catalyst on the reaction of methanol with silicon to form methoxysilanes was evaluated. For each sample tested, about 0.1 g of ground metallurgical grade silicon was transferred to a graduate cylinder. The silicon had a particle size of less than 320 mesh. Five milligrams of the copper compound and/or $NH_4HF_2$ was added to the graduate cylinder. About 0.43 ml of methanol was added to the graduate cylinder and the contents shaken to form a slurry. The slurry was quickly transferred to a thick walled Pyrex Brand tube and then chilled in dry ice to about $-78°$ C. The tube containing the mixture was purged with argon and sealed. The tubes were then heated in a tube furnace at 150° C. for the times presented in Table 1.

At the end of proscribed heating period each tube was removed from the furnace, cooled to room temperature, chilled in a dry ice bath to about $-78°$ C., then opened and the contents transferred to a vial for analysis. For analysis, each sample was centrifuged and the liquid supernate analyzed by gas liquid chromatography using a mass spectrometer as a detector (GLC-MS). The results of this analysis are presented in Table 1.

The time, in hours (h), that the sample was heated at 150° C. is presented in the first column of Table 1. The column labelled "Cat./Act." lists the copper compounds tested as catalyst and/or the acid hydrofluoride salt serving as an activator for the process. The percent conversion of methanol is presented in the column labelled "% Conv. MeOH." The area percent of alkoxsilanes formed by the process, as determined by GLC-MS, is presented under the columns labelled "Area % Product."

TABLE 1

Effects of Copper Catalyst And an Acid Hydrofluoride Salt on The Reaction of Methanol with Silicon.

| Time (h) | Cat./Act. | % Conv. MeOH | Area % Product | | |
|---|---|---|---|---|---|
| | | | $(MeO)_2SiH_2$ | $(MeO)_3SiH$ | $(MeO)_4Si$ |
| 3 | None | 0 | — | — | — |
| 3 | $CuCl_2$ | 0 | — | — | — |
| 3 | $CuF_2$ | 0 | — | — | — |
| 3 | CuO | 0 | — | — | — |
| 3 | CuBr | 0 | — | — | — |
| 3 | $NH_4Cl$ | 0 | — | — | — |
| 3 | $CuSO_4$ | 0 | — | — | — |
| 2 | $NH_4HF_2$ | 13 | — | 62 | 27 |
| 10 | $NH_4HF_2$ | 50 | — | 68 | 24 |
| 2 | $CuCl_2/NH_4HF_2$ | 56 | — | 61 | 24 |
| 2 | $CuCl/NH_4HF_2$ | 29 | — | 74 | 21 |
| 3 | $CuCl/NH_4HF_2$ | 54 | — | 88 | 11 |
| 4 | $CuCl/NH_4HF_2$ | 81 | — | 82 | 13 |
| 5 | $CuCl/NH_4HF_2$ | 100 | — | 89 | 9 |

The data presented in Table 1 demonstrate that, under the process conditions, methanol does not react with silicon in the presence or absence of copper to form methoxysilanes. Under the process conditions, when methanol is contacted with silicon in the presence of $NH_4HF_2$ methoxysilanes are formed and the rate of formation of methoxysilanes is increased when a copper compound is added as a catalyst.

EXAMPLE 2

The effect of using atomized silicon as a starting material for the process was evaluated. The atomized silicon was prepared in a manner similar to that described in Liles, U.S. Pat. No. 4,701,289, issued Oct. 20, 1987. The process of contacting the atomized silicon with methanol was similar to that of Example 1. The results are presented in Table 2. The headings of Table 2 are the same as for Table 1.

TABLE 2

Reaction of Atomized Silicon With Methanol in The Presence of Copper And an Acid Hydrofluoride Salt.

| Time (h) | Cat./Act. | % Conv. MeOH | Area % Product | | |
|---|---|---|---|---|---|
| | | | $(MeOH)_2SiH_2$ | $(MeO)_3SiH$ | $(MeO)_4Si$ |
| 3 | None | 0 | — | — | — |
| 1 | $CuCl/NH_4HF_2$ | 0 | — | — | — |
| 2.0 | $CuCl/NH_4HF_2$ | 49 | — | 73 | 20 |
| 2.5 | $CuCl/NH_4HF_2$ | 63 | — | 62 | 11 |
| 2.5 | $CuCl/NH_4HF_2$ | 80 | — | 84 | 28 |

These results, when compared to the data presented in Table 1, demonstrate that the atomized silicon is more reactive than ground silicon in the presence of CuCl and $NH_4HF_2$.

EXAMPLE 3

Hydrogen fluoride gas was bubbled through liquid methanol to form a solution of hydrogen fluoride. The methanol solution of hydrogen fluoride was contacted with ground metallurgical grade silicon and atomized silicon in the presence of CuCl to produce methoxysilanes. The ground metallurgical grade silicon was the same as that described in Example 1 and the atomized silicon was the same as described in Example 2. In addition, a sample of silicon alloy with two weight percent copper and atomized as described in Example 2, was tested. The reaction procedure was similar to that described in Example 1. The normality of the hydrogen fluoride in the methanol was determined by titration.

The results are presented in Table 3. The type of silicon is designated as: (B) ground metallurgical grade silicon, (C) atomized silicon, and (E) atomized silicon-copper alloy. The hydrogen fluoride normalities tested are presented in Table 3 under the heading "NF Norm.". All other heading are as previously described for Table 1.

The data of Table 4 demonstrate that particle size, within the range tested, had little effect on the described process.

TABLE 3

Effects of Hydrogen Fluoride Solution in Methanol on Methoxysilane Formation in The Presence of Copper Compound.

| Si Type | Time (h) | Cat./Act. | HF Norm. | % Conv. MeOH | Area % Product | | |
|---|---|---|---|---|---|---|---|
| | | | | | $(MeO)_2SiH_2$ | $(MeO)_3SiH$ | $(MeO)_4Si$ |
| B | 5 | — | 0.4 | 31 | 16 | 63 | 12 |
| B | 11 | — | 0.4 | 83 | 6 | 79 | 13 |
| B | 6 | — | 0.5 | 35 | 14 | 70 | 16 |
| B | 13 | — | 0.5 | 78 | 4 | 82 | 13 |
| B | 2.5 | CuCl | 0.15 | 30 | 6 | 64 | 18 |
| B | 5.5 | CuCl | 0.15 | 100 | 7 | 79 | 10 |
| B | 2 | CuCl | 0.5 | 21 | 17 | 62 | 12 |
| B | 3.5 | CuCl | 0.5 | 57 | 11 | 67 | 14 |
| B | 5 | CuCl | 0.5 | 93 | 8 | 75 | 10 |
| B | 5.5 | CuCl | 0.5 | 100 | 7 | 73 | 14 |
| C | 1 | CuCl | 0.5 | 53 | 10 | 70 | 12 |
| C | 2 | CuCl | 0.5 | 85 | 10 | 75 | 10 |
| E | 1.5 | CuCl | 0.15 | 46 | 15 | 68 | 12 |
| E | 2.5 | CuCl | 0.15 | 93 | 5 | 78 | 13 |
| E | 1 | CuCl | 0.5 | 35 | 2 | 72 | 17 |
| E | 2 | CuCl | 0.5 | 60 | 11 | 62 | 14 |

The data presented in Table 3 demonstrate the effectiveness of a solution of hydrogen fluoride in methanol in facilitating the reaction of methanol with silicon, both in the presence and absence of copper catalyst. Only minor differences are noted in the reaction rates and product distribution when the process is run with between 0.15 and 0.5 normality hydrogen fluoride. Of particular significance is the production of dimethoxysilane when a solution of hydrogen fluoride is used to activate the silicon.

EXAMPLE 4

The effect of the size of the silicon particles on the reaction with methanol was evaluated. The silicon tested was an atomized silicon-copper alloy containing one weight percent copper, prepared as described in Example 2. The particulate silicon was screened into the size ranges described in Table 4. The particulate silicon was contacted with methanol containing 0.3N hydrogen fluoride and 5 weight percent CuCl, based on the weight of silicon, by the procedure described in Example 1. The reaction temperature was 150° C. The percent of original methanol remaining in the reaction tube at various times was assayed by GLC-MS. The results are presented in Table 4 in the column labelled "% Conv. MeOH."

TABLE 4

Effect of Silicon Particle Size on Reaction With Methanol in The Presence of Hydrogen Fluoride and Copper Catalyst.

| Size Si (Mesh) | Time (h) | % Conv. MeOH |
|---|---|---|
| 60–100 | 0.5 | 27 |
| 60–100 | 1.5 | 65 |
| 60–100 | 2.0 | 79.5 |
| 60–100 | 3.0 | 100 |
| 100–200 | 0.5 | 29.2 |
| 100–200 | 1.0 | 42 |
| 100–200 | 2.0 | 76.7 |
| 100–200 | 3.0 | 100 |
| ≧325 | 1.0 | 48.3 |
| ≧325 | 1.5 | 67.5 |
| ≧325 | 2.0 | 82.4 |

EXAMPLE 5

The reaction of metallurgical grade silicon with isopropyl alcohol in the presence of hydrogen fluoride, with and without copper catalyst was evaluated. The process was conducted similar to that described in Example 1. Ground metallurgical grade silicon was contacted with isopropyl alcohol at a molar ratio of silicon to isopropyl alcohol of two and at a temperature of 150° C. The isopropyl alcohol contained 0.4N hydrogen fluoride in solution, prepared by bubbling hydrogen fluoride gas through the alcohol. CuCl was added as catalyst at a concentration of two weight percent, based upon the weight of silicon. The percent of the original isopropyl alcohol remaining in the sample tube at various times was determined by GLC-MS. The results are expressed in Table 5 under the heading "% Conv. i-PrOH."

TABLE 5

Reaction of Silicon With Isopropyl Alcohol in The Presence of Hydrogen Fluoride and Copper Catalyst.

| Cat./Act. | Time (Day) | % Conv. i-PrOH |
|---|---|---|
| —/— | 4 | 0 |
| —/HF | 2 | 25 |
| —/HF | 2.5 | 30 |
| —/HF | 3 | 35 |
| —/HF | 4 | 48 |
| CuCl/HF | 0.8 | 21 |
| CuCl/HF | 1.5 | 34 |
| CuCl/HF | 2 | 46 |

EXAMPLE 6

The reaction of metallurgical grade silicon with normal propyl alcohol in the presence of hydrogen fluoride, with and without copper catalyst was evaluated. The process was conducted similar to that described in Example 1. Ground metallurgical grade silicon was contacted with n-propyl alcohol at a molar ratio of silicon to n-propyl alcohol of two and at a temperature of 150° C. The n-propyl alcohol contained 0.4N hydrogen fluoride in solution, prepared by bubbling hydrogen fluoride through the alcohol. CuCl was added as catalyst at a concentration of two weight percent, based upon the weight of silicon. The percent of the original n-propyl alcohol remaining in the sample tube at various times was determined by GLC-MS. The results are expressed in Table 5 under the heading "% Conv. n-PrOH."

TABLE 6

Reaction of Silicon With n-Propyl Alcohol in
The Presence of Hydrogen Fluoride and Copper Catalyst.

| Cat./Act. | Time (h) | % Conv. n-PrOH |
|---|---|---|
| /HF | 8 | 34 |
| /HF | 16 | 68 |
| /HF | 24 | 99 |
| CuCl/HF | 5 | 41 |
| CuCl/HF | 8 | 80 |
| CuCl/HF | 10 | 97 |

What is claimed is:

1. A process for preparing alkoxysilanes of formula $$(RO)_n SiH_{4-n}$$

where R is a primary or secondary alkyl radical and n=2, 3, or 4; the process consisting essentially of: contacting silicon with a solution of hydrogen fluoride in a liquid alcohol of formula

ROH.

where R is as previously described; at a temperature within a range of 50° C. to 300° C.

2. A process according to claim 1, where the temperature is within a range of 100° C. to 200° C.

3. A process according to claim 1, where concentration of hydrogen fluoride in the liquid alcohol is within a range of 0.01N to 6.0N.

4. A process according to claim 1, where the silicon is atomized silicon.

5. A process according to claim 1, where the liquid alcohol is methanol.

6. A process according to claim 1, where the liquid alcohol is ethanol.

7. A process according to claim 1, where the alkoxysilane is a trialkoxysilane.

8. A process according to claim 1, where the alkoxysilane is trimethoxysilane.

9. A process according to claim 1, where the solution of hydrogen fluoride in a liquid alcohol is prepared by dissolving hydrogen fluoride gas in the alcohol at a concentration within a range of 0.01N to 6.0N.

10. A process according to claim 9, where the alkoxysilane is dimethoxysilane.

11. A process according to claim 1, where the solution of hydrogen fluoride in a liquid alcohol is formed by dissolving an acid hydrofluoride salt in the alcohol.

12. A process according to claim 11, where the acid hydrofluoride salt is $NH_4HF_2$.

13. A process for preparing alkoxysilanes of formula $$(RO)_n SiH_{4-n}$$

where R is a primary or secondary alkyl radical and n=2, 3, or 4; the process consisting essentially of: contacting silicon with a solution of hydrogen fluoride in a liquid alcohol of formula

ROH.

where R is as previously described; in the presence of a catalyst selected from the group consisting of copper and copper compounds; at a temperature of 50° C. to 300° C.

14. A process according to claim 13, where concentration of copper is within a range of 0.01 to 3.0 weight percent, of silicon weight.

15. A process according to claim 13, where the temperature is 100° C. to 200° C.

16. A process according to claim 13, where the concentration of hydrogen fluoride in the liquid alcohol is 0.01N to 6.0N.

17. A process according to claim 13, where the silicon is atomized silicon.

18. A process according to claim 13, where the liquid alcohol is methanol.

19. A process according to claim 13, where the liquid alcohol is ethanol.

20. A process according to claim 13, where the alkoxysilane is a trialkoxysilane.

21. A process according to claim 13, where the alkoxysilane is trimethoxysilane.

22. A process according to claim 13, where the solution of hydrogen fluoride in a liquid alcohol is prepared by dissolving hydrogen fluoride gas in the liquid alcohol at a concentration within a range of 0.01N to 6.0N.

23. A process according to claim 22, where the alkoxysilane is dimethoxysilane.

24. A process according to claim 13, where the solution of hydrogen fluoride in a liquid alcohol is formed by dissolving an acid hydrofluoride salt in the liquid alcohol.

25. A process according to claim 24, where the acid hydrofluoride salt is $NH_4HF_2$.

* * * * *